(12) United States Patent
Jang

(10) Patent No.: US 7,323,194 B2
(45) Date of Patent: Jan. 29, 2008

(54) HYDROPHILIC ANTIMICROBIAL COMPOSITION FOR AN AIR CONDITIONER EVAPORATOR OF A VEHICLE

(75) Inventor: Byeong Moo Jang, Suwon-si (KR)

(73) Assignee: Hyundai Motor Company, Seocho-Ku (KR)

( * ) Notice: Subject to any disclaimer, the term of this patent is extended or adjusted under 35 U.S.C. 154(b) by 127 days.

(21) Appl. No.: 11/180,256

(22) Filed: Jul. 13, 2005

(65) Prior Publication Data
US 2006/0013881 A1 Jan. 19, 2006

(30) Foreign Application Priority Data
Jul. 13, 2004 (KR) ........................ 10-2004-0054409

(51) Int. Cl.
*A01N 35/02* (2006.01)
*A01N 59/16* (2006.01)
*A01N 31/02* (2006.01)
*A61L 2/18* (2006.01)

(52) U.S. Cl. ...................... 424/604; 424/489; 424/641; 424/76.8; 424/76.9; 424/78.08; 514/693; 514/698; 514/738; 514/772.2; 422/5; 422/28

(58) Field of Classification Search ................ 424/489, 424/604, 76.8, 76.9, 641, 78.08; 514/693, 514/698, 738, 772.2; 422/5, 28
See application file for complete search history.

*Primary Examiner*—John Pak
(74) *Attorney, Agent, or Firm*—Morgan Lewis & Bockius LLP

(57) ABSTRACT

The present invention relates to a hydrophilic antimicrobial coating composition for an air conditioner evaporator of a vehicle with improved durability. In one embodiment of the present invention, the antimicrobial composition comprises a hydrophilic organic polymer with molecular weight in the range of about 4,000 to 8,000, a smoothing agent, an antimicrobial agent, and deionized water. In particular, the degree of polymerization between the hydrophilic functional group and a crosslinking group of the hydrophilic organic polymer is greatly improved. The antimicrobial composition is prepared with particles with a diameter of a few nanometers, which increases the number of particles per unit area and reduces the decomposition rate of the coated layer.

2 Claims, 3 Drawing Sheets

HYDROPHILIC ANTIMICROBIAL COMPOSITION FOR AN AIR CONDITIONER EVAPORATOR OF A VEHICLE

CROSS REFERENCE TO RELATED APPLICATIONS

This application is based on, and claims priority to Korean Application No. 2004-0054409, filed on Jul. 13, 2004, the disclosure of which is hereby incorporated by reference in its entirety.

TECHNICAL FIELD OF THE INVENTION

The present invention generally relates to a hydrophilic antimicrobial composition for an air conditioner evaporator of a vehicle. More specifically, the present invention relates to a hydrophilic antimicrobial coating composition for an air conditioner evaporator of a vehicle with improved durability.

BACKGROUND OF THE INVENTION

Generally, automobiles are provided with cooling and heating equipment. The cooling equipment provides a pleasant environment in the vehicle's interior by controlling temperature, humidity and wind speed. An air conditioner represents such a cooling equipment.

An air conditioner consists of three units: a blower, an evaporator and a heater. A blower delivers inside or outside air into the vehicle's interior through a motor. The speed of the motor-driven air delivery can be controlled via three or four graded levels.

The evaporator circulates a coolant, which, after being passed through a compressor, undergoes compression and expansion processes through a belt driven by the engine. This ventilates the air that is cooled by passing through the evaporator into the interior of the vehicle after the air is delivered by the blower.

The heater unit is connected to a coolant line of the vehicle's engine. Thus, the temperature of the coolant increases as the engine becomes heated. Since the coolant is always circulated by a pump, it can be heated while the engine operates, which results in warm air being delivered into the vehicle's interior.

It is common to see a vehicle's cooling device that is provided in a unit structure that emits bad odors inside of the vehicle during the operation of the air conditioner. This occurs because all the air sent by the blower is passed through the evaporator, which is usually wet due to the presence of condensed water—a result of steam from the air condensing due to a drastic change in ambient temperature—thus providing a suitable habitat for fungi and bacteria.

The concentrated water tends to become spattered due to the increased resistance against ventilation, which is a result of the densely arranged radiation fins and an extended volume of ventilation as the vehicle's air conditioner becomes smaller and optimized. Further, when the air is contaminated with foreign materials, such as dust, fungi and bacteria, and passes through the evaporator by being delivered to the inside of a vehicle, it results in the emission of bad odors, which often becomes the cause of respiratory diseases for passengers in the vehicle.

To eliminate bad odors, a compressed aerosol type biocide or a hydrophilic-antimicrobial coating is put on the evaporator. In the case of using a compressed aerosol type biocide, the biocide is sprayed through the exterior inlet and often sticks to the blower or a passage way without reaching the target evaporator. Thus, effective biocidal activity cannot be expected. Further, the masking of bad odors by the sprayed flavors is only temporary and cannot last long. Generally, an aerosol type biocidal and deodorant spray is prepared such that the organic biocide, flavor, and deodorant are mixed with ethyl alcohol and then filled with compressed gas in a container. However, the sprayed biocide cannot reach sufficiently deep into the evaporator to clean it, so the sprayed biocide does not reach the bacteria and fungi to eradicate them.

In the case of applying a hydrophilic-antimicrobial coating on the evaporator, in which the hydrophilic-antimicrobial coating consists of inorganic hydrophilic particles, such as silicates, and an organic binder, the cracks in the coated layer can be easily peeled off when in use because silica particles are relatively large and thus not densely arranged. Further, the coating also provides a frame around the silica particles on which the bad odor-emitting particles as well as bacteria and fungi can grow. The silica particles emits a cement-like smell, which is unpleasant to the driver. In addition, $OH^-$ and $H^+$, the hydrophilic groups of the organic hydrophilic antimicrobial binder, react with water, causing the coated layer to decompose and evaporate, thereby exposing the aluminium on the evaporator. In fact, the coated layer lasts up to one or two years after delivery from the factory. These properties can be analyzed via hydrophilic durability test. The initial contact angle is about one to about eight degrees, and the contact angle after durability test is generally above 40 degrees. Therefore, due to the absence of a hydrophilic antimicrobial agent, antimicrobial and bad odors removing properties are accordingly very poor, and the air conditioning function is also deteriorated.

SUMMARY OF THE INVENTION

The present invention provides an antimicrobial composition for an air conditioner evaporator of a vehicle having hydrophilic and antimicrobial properties as well as improved durabilty. The antimicrobial composition of the present invention comprises a hydrophilic organic polymer with molecular weight in the range of about 4,000 to 8,000, a smoothing agent, an antimicrobial agent, and deionized water. In particular, the degree of polymerization between the hydrophilic functional group and a crosslinking group of the hydrophilic organic polymer is greatly improved, and the antimicrobial composition is prepared with particles with a diameter of a few nanometers, which increases the number of particles per unit area and reduces the decomposition rate of the coated layer.

BRIEF DESCRIPTION OF THE DRAWINGS

The above and other objects and features of the present invention will become apparent from the following description of the invention, when taken in conjunction with the accompanying drawings, wherein.

DETAILED DESCRIPTION OF PREFERRED EMBODIMENTS

Figure 1:
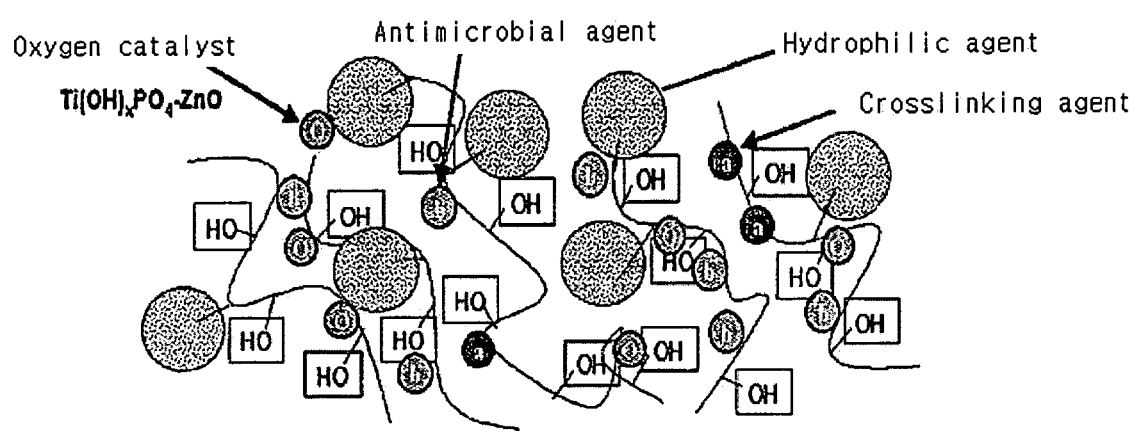
FIG. 1 shows a schematic diagram of a hydrophilic antimicrobial composition for an air conditioner evaporator of a vehicle according to an embodiment of the present invention.
Figure 2:
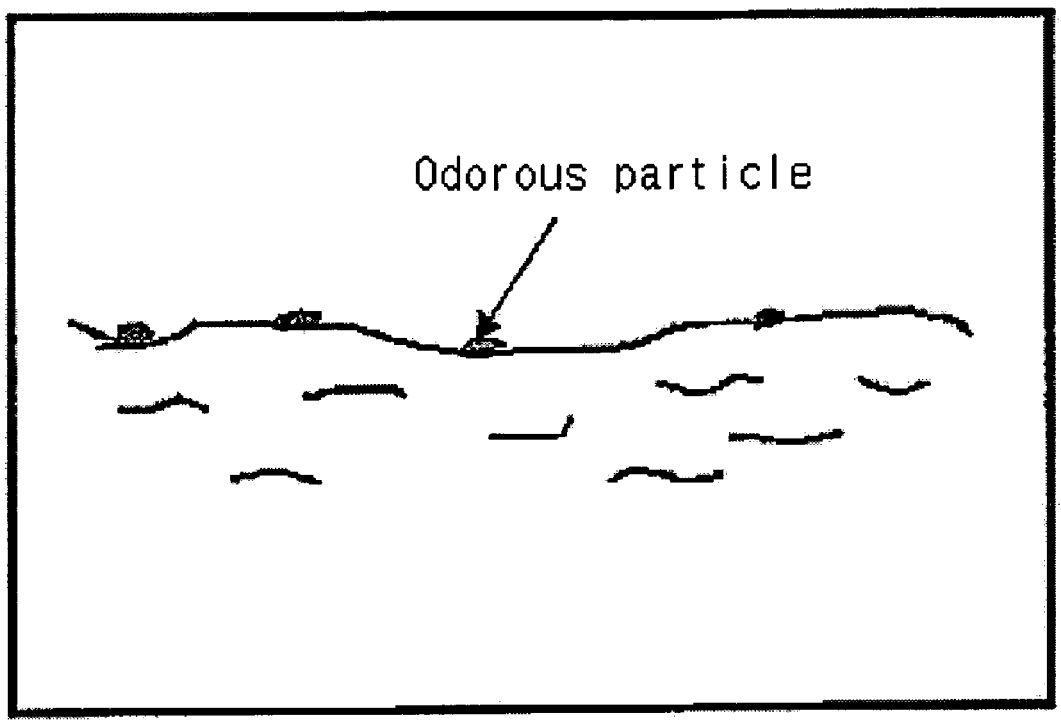
FIG. 2 shows a schematic diagram of a hydrophilic antimicrobial composition for an air conditioner evaporator of a vehicle with respect to its size according to an embodiment of the present invention.

The embodiments of the present invention provides a hydrophilic and antimicrobial composition for an air conditioner evaporator of a vehicle comprising a hydrophilic polymer, a smoothing agent, an antimicrobial agent and deionized water thereby removing bad odors emitted in typical coating compositions themselves while improving durability and exhibiting an antimicrobial effect.

More specifically, the present invention employs a hydrophilic organic polymer having a molecular weight of about 4,000 to about 8,000 as a component for the antimicrobial composition to improve durability and remove bad odors intrinsic to traditional type of coating compositions. The degree of polymerization between a hydrophilic functional group and a crosslinking agent is also improved. Further, the particle size of the antimicrobial composition is ultrafine with a diameter ranging from about $5 \times 10^{-9}$ to about $9 \times 10^{-9}$ m, which increases the number of particles per unit area thereby delaying the decomposition rate of the hydrophilic group or antimicrobial agent.

In one embodiment of the present invention, about 10 to about 15 wt % of polyvinylalcohol, about 5 to about 8 wt % of diethyleneglycol, and about 3 to about 5 wt % of polyethyleneglycol are mixed together to form the hydrophilic organic polymers for the antbacterial composition. If polyvinyl alcohol content is less than 10 wt %, it results in a decrease in initial and durable hydrophilicity. On the other hand, it results in a deterioration in the antimicrobial property and coating uniformity, if the polyvinyl content exceeds 15 wt %. If the diethyleneglycol content is less than 5 wt %, it results in decreased functionality as a supplemental hydrophilic agent for the polyvinyl alcohol. Yet, it results in a deterioration in the antimicrobial property and coating uniformity, if the diethyleneglycol content exceeds 8 wt %. If the polyethyleneglycol content is less than 3 wt %, it results in a decreased degree of polymerization of the polyvinylalcohol. Conversely, it results in a deterioration in the antimicrobial properties and coating uniformity, if the polyethyleneglycol content exceeds 5 wt %.

In addition, other conventional compounds that can improve smoothness may be added in this antimicrobial composition, and diethyloctanediol is used as a smoothing agent in an embodiment of the present invention. About 1 to about 3 wt % of the above smoothing agent is added. If there is less than 1 wt % of the smoothing agent, then it cannot exhibit any noticeable effect. When the smoothing agent content exceeds 3 wt %, it generates foams during the coating process.

Acetaldehyde and $Ti(OH)_X(PO_4)_Y$—ZnO particles are used as an antimicrobial agent in the present invention. The $Ti(OH)_X(PO_4)_Y$—ZnO particles have a diameter size of about $2 \times 10^{-12}$ to about $9 \times 10^{-12}$ m, wherein X is an integer of 2 to 4 and Y is an integer of 1 to 4. When $Ti(OH)_X(PO_4)_Y$—ZnO particles are in contact with oxygen or water, it results in a surface reaction and thus generates active divalent oxygen, which is very unstable. This leads to a reductive reaction to receive electrons and also generates hydrogen peroxide. The hydrogen peroxide becomes a hydroxyl radical capable of strong oxidative reaction, which decomposes the organics and eliminates fungi and bacteria.

In the present invention, acetaldehyde and $Ti(OH)_X(PO_4)_Y$—ZnO particles are used together to further improve the hydrophilic antimicrobial composition about 1 to About 2 wt % of acetaldehyde is added in this embodiment of the present invention. If the acetaldehyde content is less than 1 wt %, then it cannot exhibit good antimicrobial effect while it becomes toxic to humans if its content exceeds 2 wt %. About 7 to about 10 wt % of $Ti(OH)_X(PO_4)_Y$—ZnO particles are added. If the $Ti(OH)_X(PO_4)_Y$—ZnO particle content is less than 7 wt %, then it results in decreased activation of the red-ox reaction of particles of the composition. Yet, if the $Ti(OH)_X(PO_4)_Y$—ZnO particle content exceeds 10 wt %, then it may decrease its smoothing effect.

The aforementioned components of the antimicrobial composition of the present invention are dissolved in deionized water. About 50 to about 70 wt % of deionized water is added. If the deionized water content is less than 50 wt %, it is difficult to dissolve solid components of this composition. However, if the deionized water content exceeds 70 wt %, then it will decrease the hydrophilic and antimicrobial properties.

As stated above, the hydrophilic and antimicrobial composition of the present invention exhibits excellent durability and hydrophilic and antimicrobial properties. This composition is suitable as a coating for an air conditioner evaporator of a vehicle.

The present invention is explained in more detail based on the following Examples however they should not be construed as limiting the scope of the present invention.

EXAMPLE

Example 1 and Comparative Example 1

Hydrophilic coating compositions were prepared according to the composition and contents as shown in the following Table 1. The biocidal effect and durability of the prepared compositions were measured according to the methods described below and the results are shown in Table 1.

Method of Measurement

1. Antimicrobial Property

1) Test for Antifungal Effect

A glass plate is coated with fungi with a predetermined thickness, in which the specimen is covered and kept for 3 weeks at 25° C. with about 60 to 100% humidity. Fungi growth on the specimen was observed.

(Criteria of Evaluation)

Level 0: No growth of Fungi
Level 1: 10% growth of Fungi
Level 2: 10 to 30% growth of Fungi
Level 3: 30 to 60% growth of Fungi
Level 4: over 60% growth of Fungi 2) Test of Antibacterial Effect Bacteria types to be tested were determined. They were stored at −50° C. in the freezer and then transferred to a refrigerator at 5° C. twelve hours prior to the test. First, a culturing media for the selected bacteria was prepared. The culturing media was mixed with the selected bacteria with a predetermined number of bacteria and cultured without addition of any test specimen (i.e., blank) for 24 hours at 37° C. with 95% humidity, and the number of bacteria was counted. Then, the mixture of the culturing media and the selected bacteria (the number of bacteria was counted before placing them on the specimen) were placed on top of testing specimen and cultured for 24 hours at 37° C. with 95% humidity, and the resulting number of bacteria was counted to observe the specimen's effect on bacteria growth.

2. Test of Hydrophilicity

1) Initial Contact Angle

Figure 3:
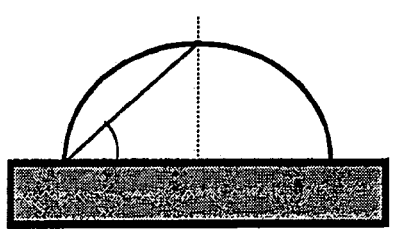
FIG. 3 shows a schematic diagram of a method for measuring initial contact angle as a hydrophilicity test for a hydrophilic antimicrobial composition for an air conditioner evaporator of a vehicle according to an embodiment of the present invention.
Figure 4:
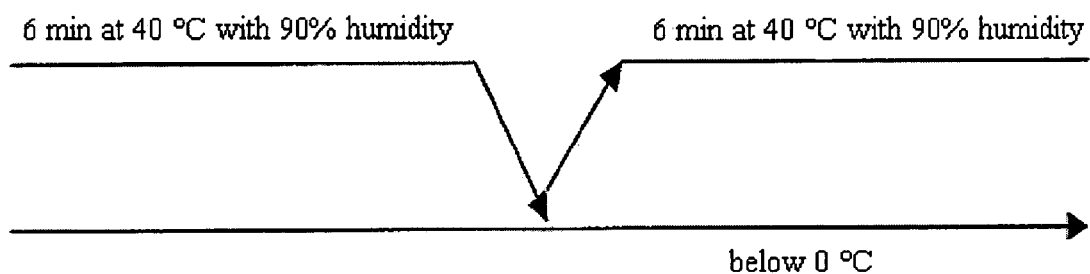
FIG. 4 shows a schematic diagram of a method for measuring durable contact angle as a hydrophilicity test for a hydrophilic antimicrobial composition for an air conditioner evaporator of a vehicle according to an embodiment of the present invention.

After dropping 0.05 cc of water to a test area, the 'q' angle is measured within about eight to ten seconds using a contact angle measurer as shown in FIG. 3. Then, the value of "2q" is read as the "contact angle." The height of dropping water is close to "0."

2) Durable Contact Angle

The specimen was maintained for 6 minutes at 40° C. with relative humidity of more than 90%, cooled down to below 0° C. at the rate of −10° C./min, then immediately heated at the rate of 10° C./min to reach 40° C., and maintained for 6 minutes at 40° C. with about 90% humidity. The entire process of the above steps is considered as one cycle, and durable contact angle is measured through the same method as in the method used in measuring initial contact angle after repeating 500 cycles.

3. Odor Test

1) Under Dry Conditions

After setting up standard testing conditions at room temperature, the evaporator to be tested was installed inside the testing equipment. Then, an air blower was operated to maintain a wind-passing rate of 1 m/sec at the test area, and emissions analysis was performed to detect the presence and level of any odors.

2) Under Wet Conditions

After being placed for 72 hours at an outdoor air temperature of 40° C. with relative humidity of more than 90%, the evaporator to be tested was installed inside the testing equipment. Then, an air blower was operated to maintain the wind-passing rate of 1 m/sec at the test area and emissions analysis was performed to detect the presence and level of any odors. Before installing the evaporator into the testing equipment, it is fully wetted with water over its entire surface.

3) Criteria for Odor Test (Emissions Analysis: More Than 10 Persons)

Intensity of Odor

Level 1: Strong odor

Level 2: Apparent presence of odor

Level 3: Mild odor

Level 4: Very mild odor

Level 5: No odor

Comparative Example 2

The conventional types of coating compositions were tested for their antimicrobial property and durability as in Example 1. The results are shown in table 1.

TABLE 1

| Classification (wt %) | | Example 1 | Comp. Ex. 1 | Comp. Ex. 2 |
|---|---|---|---|---|
| Hydrophilic Polymer | Polyvinylalcohol | 12 | 7 | Hydrophilic agent: inorganic silicate ($SiO_2$): 10-20% of other organic binder |
| | Diethyleneglycol | 7 | 3 | |
| | Polyethyleneglycol | 4 | 3 | |
| Smoothing agent | Diethyloctanediol | 2 | 2 | |
| Antimicrobial agent | Acetaldehyde | 2 | 2 | |
| | $Ti(OH)_X(PO_4)_Y$—ZnO | 9 | 4 | |
| Deionized water | | 64 | 79 | Remnant |
| Physical properties | Antimicrobial property | (1) Antifungal property: Level 0 (2) Rate of Bacterial Reduction: 99.9% | (1) Antifungal property: Level 1 (2) Rate of Bacterial Reduction: 85% | (1) Antifungal property: Level 0 (2) Rate of Bacterial Reduction: 90% |
| | Hydrophilic contact angle | Initial: 2° Durable: 15° | Initial: 7° Durable: 35° | Initial: 5° Durable: 28° |
| | Odor | Level 0 | Level 3 | Level 3-4 |

As shown in the above table 1, the antimicrobial coating composition of the present invention shows improvements in terms of antimicrobial activities, hydrophilicity and odors. Further, it is also shown in the Comparative Example 1 that the coating antimicrobial composition having a performance range outside of that of the present invention cannot effectively perform the desired activities.

The invention has been described in detail with reference to preferred embodiments thereof. However, it will be appreciated that those skilled in the art, upon consideration of the disclosure, may make modifications and improvements within the scope and spirit of the invention.

What is claimed is:

1. A hydrophilic antimicrobial composition for an air conditioner evaporator of a vehicle comprising:
    about 10 to about 15 wt % of polyvinylalcohol;
    about 5 to about 8 wt % of diethyleneglycol;
    and about 3 to about 5 wt % of polyethyleneglycol;
    about 1 to about 3 wt % of diethyloctanediol as smoothing agent;
    about 1 to about 2 wt % of acetaldehyde and about 7 to about 10 wt % of $Ti(OH)_X(PO_4)_Y$—ZnO having a particle size of about $2\times10^{-12}$ to about $9\times10^{-12}$ m, both as antimicrobial agent, wherein X is an integer of 2 to 4 and Y is an integer of 1 to 4; and
    about 50 to about 70 wt % of deionized water.

2. The hydrophilic antimicrobial composition for an air conditioner evaporator of a vehicle according to claim 1, wherein said polyvinylalcohol, said diethylene glycol and said polyethyleneglycol are mixed together.

* * * * *